United States Patent
Tekalur et al.

(10) Patent No.: US 11,914,801 B2
(45) Date of Patent: Feb. 27, 2024

(54) TREMOR CANCELLATION

(71) Applicant: EATON INTELLIGENT POWER LIMITED, Dublin (IE)

(72) Inventors: Srinivasan Arjun Tekalur, Okemos, MI (US); Sourav Dutta, Dublin (IE)

(*) Notice: Subject to any disclaimer, the term of this patent is extended or adjusted under 35 U.S.C. 154(b) by 0 days.

(21) Appl. No.: 17/907,333

(22) PCT Filed: Mar. 26, 2020

(86) PCT No.: PCT/EP2020/058519
§ 371 (c)(1),
(2) Date: Sep. 26, 2022

(87) PCT Pub. No.: WO2021/190752
PCT Pub. Date: Sep. 30, 2021

(65) Prior Publication Data
US 2023/0112139 A1   Apr. 13, 2023

(51) Int. Cl.
*G06F 3/038* (2013.01)
*G06F 18/2415* (2023.01)
*G06F 3/0338* (2013.01)
*G06F 3/0354* (2013.01)

(52) U.S. Cl.
CPC .......... *G06F 3/038* (2013.01); *G06F 3/0338* (2013.01); *G06F 3/03543* (2013.01); *G06F 3/03547* (2013.01); *G06F 18/2415* (2023.01)

(58) Field of Classification Search
CPC .... G06F 3/038; G06F 3/0338; G06F 3/03543; G06F 3/03547; G06F 18/2415
See application file for complete search history.

(56) References Cited

U.S. PATENT DOCUMENTS

| | | | |
|---|---|---|---|
| 6,561,993 B2 | 5/2003 | Adapathya et al. | |
| 2002/0120217 A1* | 8/2002 | Adapathya | G06F 3/038 600/595 |
| 2005/0219213 A1* | 10/2005 | Cho | G06F 3/0346 345/158 |
| 2005/0243061 A1* | 11/2005 | Liberty | G06F 3/017 345/158 |

(Continued)

FOREIGN PATENT DOCUMENTS

WO   2004/059560 A2   7/2004

*Primary Examiner* — Ariel A Balaoing
(74) *Attorney, Agent, or Firm* — LEYDIG, VOIT & MAYER, LTD.

(57) ABSTRACT

A user interface device is adapted to provide tremor cancellation. The user interface device comprises a user interface for determining a position from a physical user input and a position output for providing a time-ordered output stream of position data, but also provides a tremor learning module and a tremor cancellation module. The tremor learning module can be trained to identify tremor patterns for a user by comparing time-ordered output streams of position data produced by the user with predetermined representations. The tremor cancellation module is adapted to apply the tremor patterns learned for the user to cancel tremors in a time-ordered stream of position data produced by the user to create an output stream of position data which is corrected for user tremor. A method of training and then using such a user interface device is also described.

14 Claims, 9 Drawing Sheets

(56) References Cited

U.S. PATENT DOCUMENTS

| | | | |
|---|---|---|---|
| 2006/0152740 A1* | 7/2006 | Cavallucci | G06F 3/0421 |
| | | | 356/614 |
| 2006/0178212 A1* | 8/2006 | Penzias | G06F 3/01 |
| | | | 715/863 |
| 2012/0007821 A1* | 1/2012 | Zaliva | G06F 3/04166 |
| | | | 345/173 |
| 2012/0229385 A1* | 9/2012 | Fu | G06F 3/0346 |
| | | | 345/163 |
| 2018/0032159 A1 | 2/2018 | Pathak et al. | |
| 2018/0173268 A1* | 6/2018 | Zhao | G05G 9/047 |

* cited by examiner 61 62 63

TREMOR CANCELLATION

FIELD OF DISCLOSURE

The present disclosure relates to tremor cancellation. In particular, the disclosure relates to tremor cancellation in a human-computer interface.

BACKGROUND TO DISCLOSURE

Tremor is a form of involuntary muscle contraction and relaxation involving oscillatory or twitching movements of one or more body parts, most frequently the hands. It usually has a rhythmic component and so can be characterised to some degree clinically and for individuals. There are a number of causes, many relating to neurodegenerative diseases such as Parkinson's disease or other neurological conditions. The most common type is essential tremor, which is typically occurs at frequencies of 4-8 Hz. Also common is dystonic tremor, which results from the movement disorder dystonia. Tremor can generally not be cured, though various medications can reduce the severity of the condition in some cases.

Many sufferers from tremor can lead a normal productive life, but there are some activities that will be severely impacted by the condition. One is the use of a conventional human-computer interface. A user with tremor will be severely compromised in using a device requiring physical interaction, such as a computer mouse, a joystick or a trackpad. While these interfaces may be bypassed in some cases—for example, by using voice input—there are a number of situations (for example, computer aided design (CAD)) where this is the only practical user interface type.

Various devices have been proposed to reduce tremor by active intervention—U.S. Pat. No. 6,234,045 and WO2015/128090 teach tremor cancellation devices, and stabilizing devices are provided by companies such as Liftware—but these compromise the user's ability to interact with a user interface device effectively by the nature of their intervention. Various approaches have been taken to modifying human computer interaction with adapters (WO2015/164128), tailored environments (US2009/0089718) and device drivers (U.S. Pat. No. 6,561,993), but these involve a significant intervention in the user's computing environment and are generally visible or otherwise apparent to others. This affects the privacy of the user and makes their impairment apparent to others. It would be highly desirable to achieve a solution that allowed a user with tremor to use a physical user interface effectively in a way that preserved user privacy and did not make the nature of their condition apparent to others.

SUMMARY OF DISCLOSURE

In a first aspect, the disclosure provides a user interface device for tremor cancellation, the user interface device comprising: a user interface for determining a position from a physical user input; a tremor learning module; a tremor cancellation module; and a position output for providing a time-ordered output stream of position data; wherein
the tremor learning module is adapted to be trained to identify tremor patterns for a user by comparing time-ordered output streams of position data produced by the user with predetermined representations; and the tremor cancellation module is adapted to apply the tremor patterns learned for the user to cancel tremors in a time-ordered stream of position data produced by the user to create an output stream of position data which is corrected for user tremor.

While tremors are involuntary, they can typically be characterised for individuals (U.S. Pat. No. 7,236,156 provides one example of a system for identifying individuals based on tremor). Tremor modelling using appropriate techniques such as Fourier linear combination (IEEE Trans Biomed Eng. 2016 November; 63(11):2336-2346. "A Quaternion Weighted Fourier Linear Combiner for Modeling Physiological Tremor", Adhikari K et al) and motion filtering with support vector machines ("Tremor Detection Using Motion Filtering and SVM", Soran B et al, in Proceedings of the 21st International Conference on Pattern Recognition (ICPR2012)) has been used for this purpose. The present approach builds on this ability to characterise a tremor to create a personalised user interface solution in which a tremor is characterised and then cancelled to allow a user input to be provided in a tremor-free form.

This the tremor learning module may comprise a machine learning model, such as a classifier, for example a perceptron. Other machine learning approaches, such as support vector machines, may be used in alternative embodiments. Here, the predetermined representations may comprise a predetermined set of patterns. An input to the machine learning model may be provided by polynomial regression of the time-ordered output streams of position data produced by the user with predetermined representations. In this case, the input to the machine learning model may comprise the order and the coefficients of the polynomial.

Such a user input device may comprise a single physical device, with all the functional elements described resident within it. This could be, for example, a mouse, a trackpad or a joystick. In this way, the user input device in use may be effectively indistinguishable from a conventional user input device of the same type, even though it has been trained to cancel or compensate for the tremor of a specific user. It may produce the same type of output as a conventional device, and it may operate using a conventional driver. While different arrangements may be required during the training phase for ease of training, during actual use (the "running phase") the user input device may appear entirely conventional both physically and logically to externally interacting people or systems.

In a second aspect, the disclosure provides a method of cancelling user tremor with a user interface device, the user interface device comprising a user interface for determining a position from a physical user input and a position output for providing a time-ordered output stream of position data, the method comprising: training a tremor learning module in the user interface device from user input for predetermined representations to obtain tremor patterns for a user; after training, when the user provides user input through the user interface, the user interface device cancels the tremor using the tremor patterns to provide a tremor-cancelled time-ordered stream of output data from the position output.

DESCRIPTION OF SPECIFIC EMBODIMENTS

Specific embodiments of the disclosure are now described, by way of example only, with reference to the accompanying drawings, of which:

Figure 1:
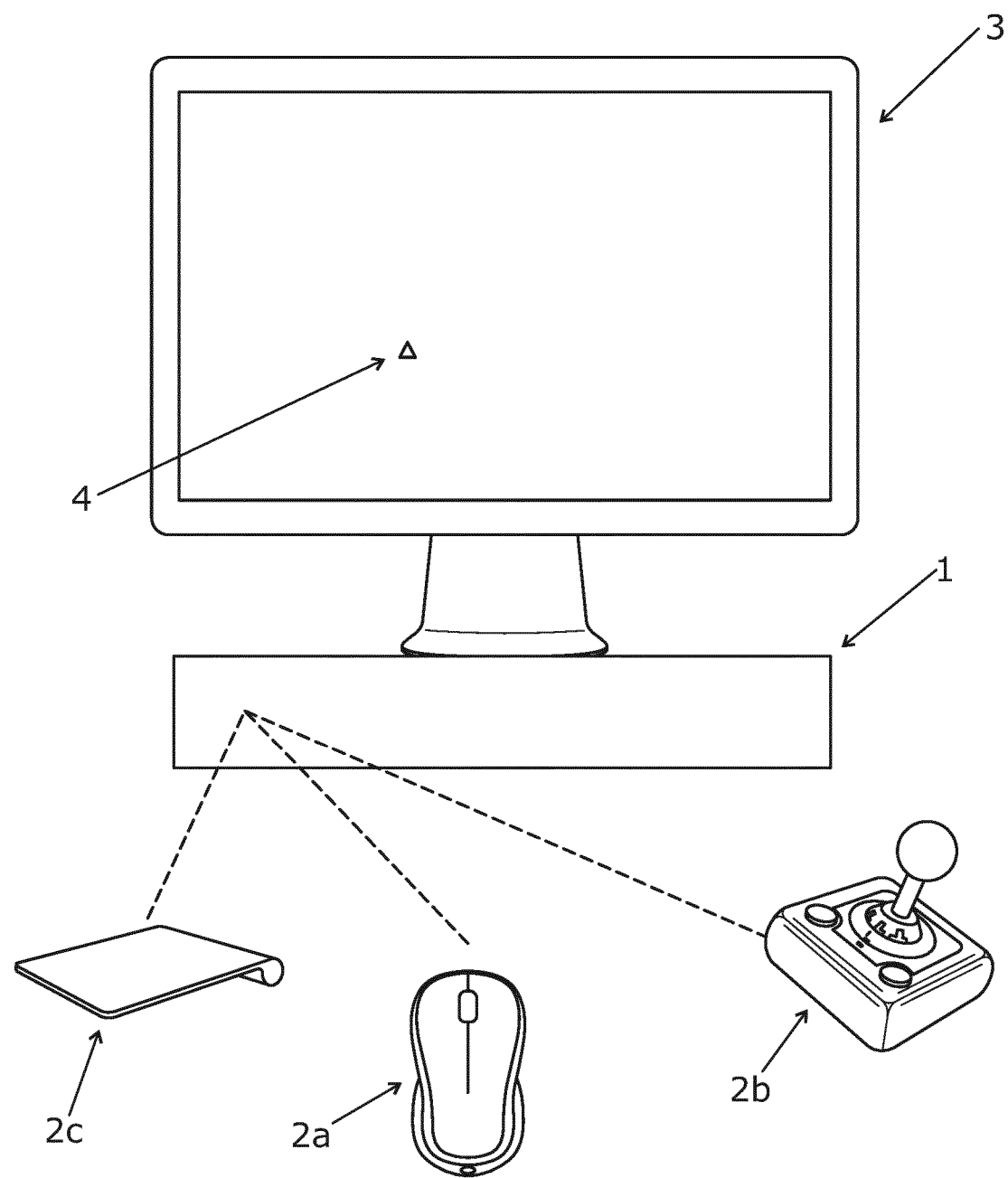
FIG. 1 shows an exemplary human-computer interface in which physical user input is used to provide position information.
Figure 2:
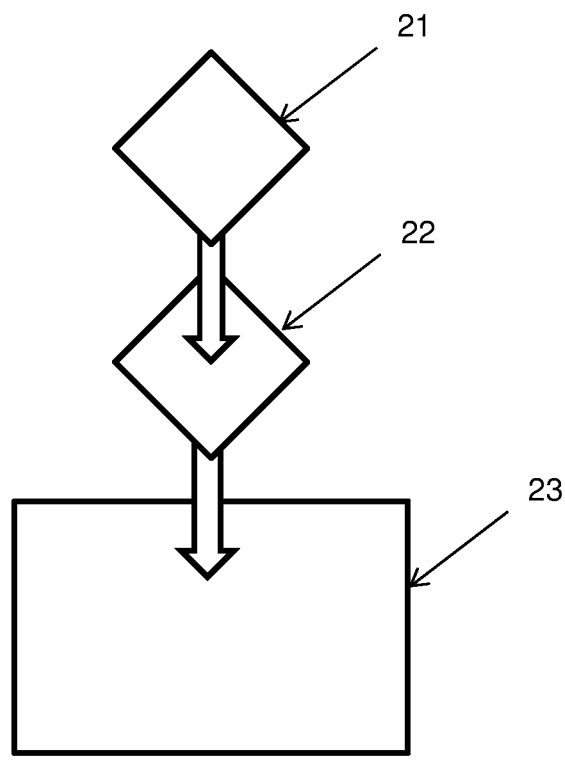
FIG. 2 shows schematically elements in a conventional physical input user interface.
Figure 3:
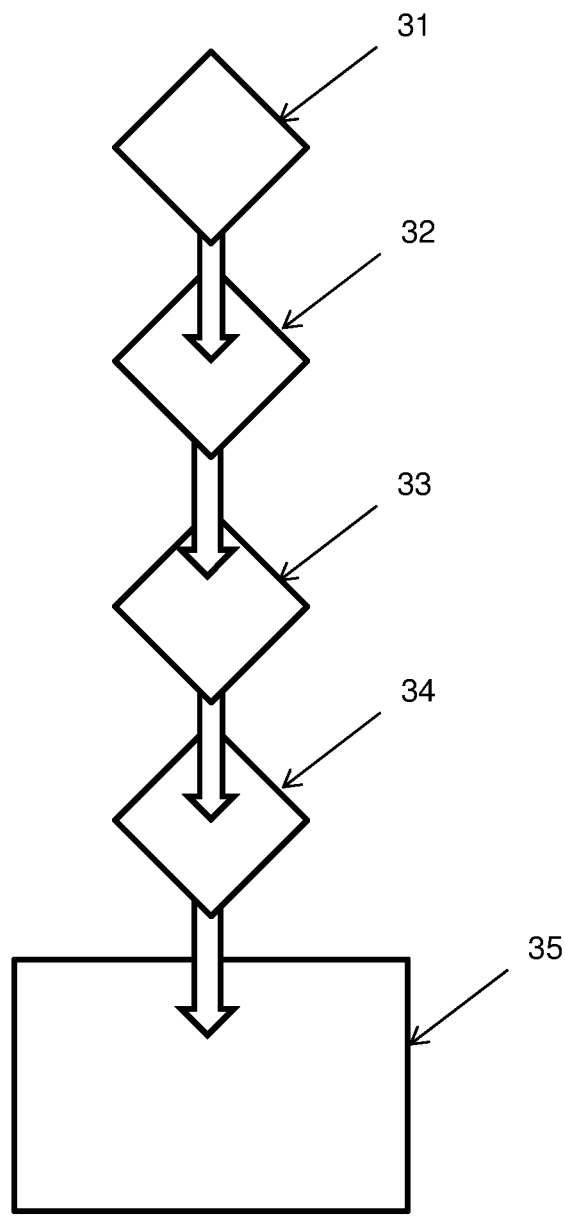
FIG. 3 shows schematically elements in a physical input user interface according to embodiments of the disclosure.
Figure 4:
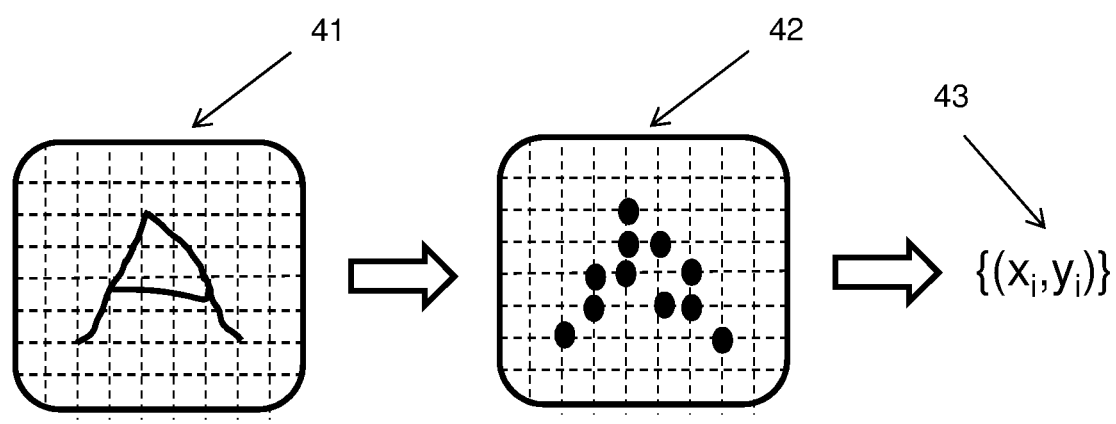
FIG. 4 shows exemplary steps performed in a user movement representation layer according to an embodiment of the disclosure.
Figure 5:
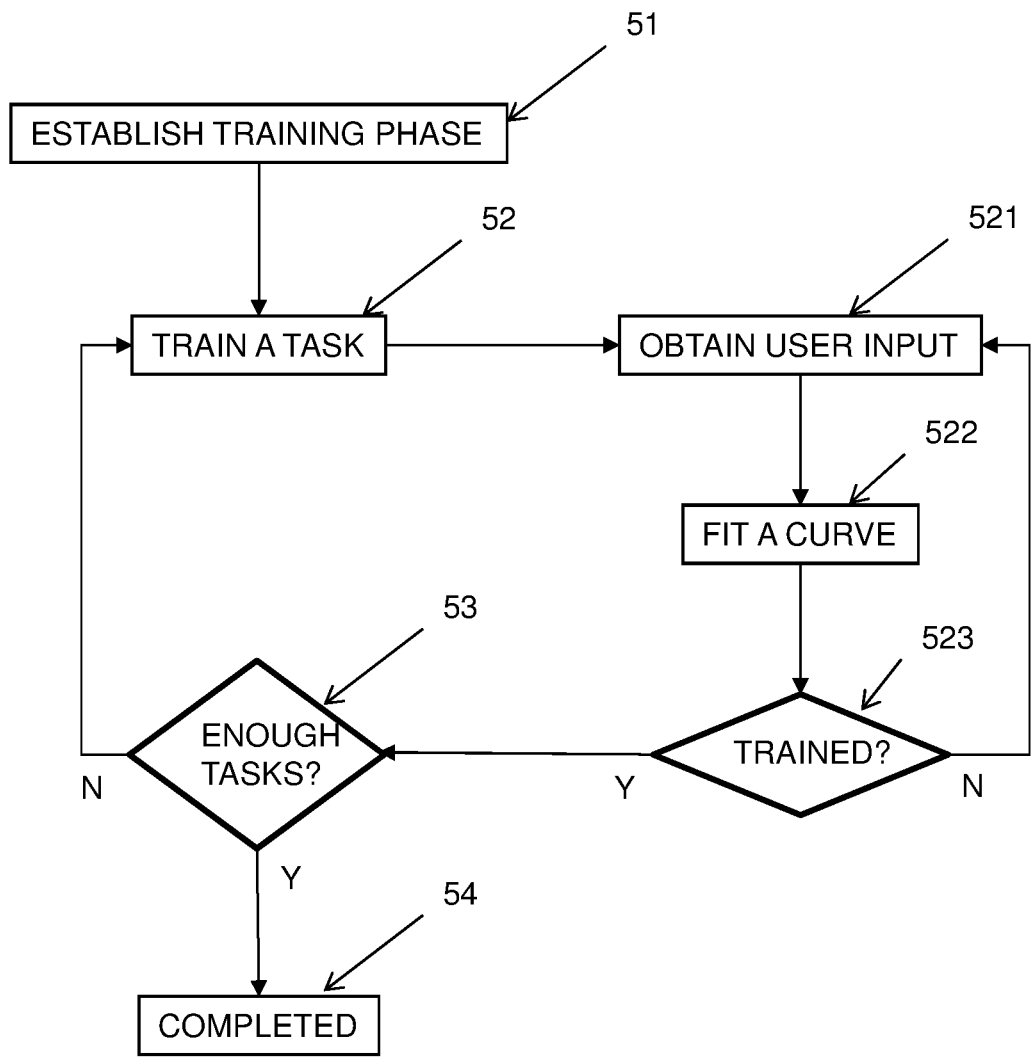
FIG. 5 shows exemplary steps performed in a training phase using a tremor learning module according to an embodiment of the disclosure.

FIG. 1 provides an illustrative context for embodiments of the disclosure. A computer 1 has an associated display 3, here showing a largely blank screen with a cursor 4.

Alternative ways of providing physical input that can be used to move the cursor 4 are provided. The first is a computer mouse 2a. The second is a joystick 2b. The third is a trackpad 2c. In each case user movement—dragging of the mouse 2a, gripping and pulling or pushing the joystick 2b, or movement of a finger or a stylus along the surface of the trackpad 2c—is translated into movement of the cursor across the display. This may be used for traversing or modifying documents or other objects rendered on the display.

These physical input devices, in their conventional form, can be represented by the same set of elements. A user input layer 21 takes a physical action and through the agency of a technology (which may be optical position detection for a mouse, or capacitive sensing for a touchpad, for example), translates that physical action into position data. The physical action will typically vary over time, and a movement capture layer 22 may be used to provide an output stream composed of position and time values. These will be translated, using the internal architecture of the device 23—which may vary for input devices of different types (and which is not relevant here, as the skilled person will be aware of appropriate conventional architectures for different input device types)—into input to the computer 1 which may be used to move the cursor 4.

In a proposed system according to an embodiment of the disclosure, the user input layer 31 is essentially the same and there is a movement capture layer 34 with different functionality, but there are also two intermediate layers. One is a movement representation layer 32—like the movement capture layer 34, this produces an output consisting of position and time pairs. In this case, however, the output of the movement representation layer 32 is not corrected for tremor, whereas the movement capture layer 34 (after a training process has taken place) will be corrected. The movement representation layer can be considered a tremor detection module 32. The next layer is a training layer which acts as a tremor learning module 33—once the process of training and learning is complete, this will also indicate what correction needs to be applied to cancel the tremor. The movement capture layer 34 now includes the function of tremor cancellation by correcting for user tremor as characterised by the tremor learning module 33, so this movement capture layer can be considered a tremor cancellation module 34. The output of the movement capture layer 34 is as before translated using the internal architecture of the device 35 into input to the computer 1 which may be used to move the cursor 4.

Preferably, each of these new or modified layers—the tremor detection module 32, the tremor learning module 33 and the tremor cancellation module 34—is implemented in hardware and built into the user input device. In this way, the user input device itself may appear indistinguishable, or as a normal design variant, of a conventional user input device of that type (without any visible "adapter"). In this way, user privacy is preserved in the user working environment.

User privacy is also preserved in the way the output of the user input device is provided, as this output is essentially the same as would be received from a tremor free user—the computer itself does not need to distinguish between the output of a user input device in accordance with the disclosure and the output of a conventional user input device of the same type. No special drivers, or intervening software layer, are required. This is because after training, the user uses the user input device in exactly the conventional way. The result of this use will be a stream of data (time and position) containing tremor—this is output by the tremor detection module 32. After training (in embodiments described below, provided by use of machine learning techniques with use of regression models), the tremor learning module 33 will have learned tremor patterns of the user. The tremor cancellation module 34 can then use these tremor patterns to cancel tremor from the initial stream to produce an output stream from which tremor has been cancelled—so the output stream is essentially the same as would be received from a tremor-free user using a conventional user input device. As the output stream will be the same in these two cases, embodiments of the disclosure can interact seamlessly with all human-computer interface solutions in a way that is not intrusive and privacy preserving as no other system modification is required.

These modules will now be described in more detail.

As previously noted, the tremor detection module 32 operates in a very similar way to a normal movement capture layer in a conventional user input device. The input layer 31 provides a signal through an appropriate technology—mechanical movement, optical detection and capacitive sensing are exemplary—and the features of the user interaction mechanism define the type of user input device (of which mouse, trackpad and joystick are non-limiting examples). The tremor detection module 32 samples the signal at the input layer 31—typically providing a stream of position and time values—and these may be represented in two dimensions (for a conventional computer interface—in principle, in three dimensions) typically by a piecewise linear function. In terms of components, nothing is needed that is not already present for a conventional user input device of the relevant type, as the only significant difference is that in a conventional user input device this layer provides the output stream from the device, whereas in this arrangement additional layers are provided.

The tremor learning module 33 has no counterpart in a conventional user input device. This component is designed to determine tremor patterns characterizing the tremor of an individual. It does this by training—the user is asked to provide, using the user input device, a series of pre-defined figures (for example, letters, numbers, symbols, lines, polygons, curves). The tremor learning module 33 uses the pre-defined figures and the piecewise linear user depictions as inputs, and it uses these inputs to distil the normal movement of the user from the user tremor by using statistical and machine learning techniques (such as regression models and classification). With sufficient training, the tremor learning module 33 builds up a personalised user tremor model. This may be a one-time step taking place before active use of the user input device, but it may also be a process which continues to be refined after the initial training to improve results.

The tremor cancellation module 34 uses the other two modules to cancel user tremor. The raw user input, as a linear piecewise representation, is received from the tremor detection module 32. The tremor patterns defined by the personalised user tremor module 33 are used in a mathematical transformation to cancel the user tremor from the piecewise linear representation produced by the tremor detection module. The output of the tremor cancellation module 34 is a tremor cancelled output stream which is similar in character to the output of the tremor detection module—the values have simply been changed to correct the tremor. From the point of view of the next element in the system, there is no difference between the output of this embodiment and the output of a conventional user input device of the same technical type.

Each of these modules may be built into a conventional user input device structure—typically using suitably programmed additional hardware, requiring for example a small additional circuit board—in such a way that the existing structure of the user input device need not be altered. As the input method and output format of the user input device can be conventional, it can be used when trained without any additional software or hardware setup. In this way, the user can use the user input device in different contexts and with different devices effectively and without compromising user privacy. Embodiments as described here are not limited to use for a single user—while training takes place for a specific user, it is possible for the device to be retrained for a different individual. It is also possible in embodiments for more than one user profile to be stored, with it being determined in use which user profile is to be used.

As indicated previously, embodiments of the disclosure may use a variety of different user input device structures. Mice, trackpads and joysticks are explicitly discussed here, but in principle the disclosure is applicable to any form of interaction between a user hand, finger, or hand-controlled object (such as a stylus) with a computer user interaction region. Embodiments of the disclosure may relate to an explicit computing device such as a tablet, laptop or personal computer, but also a multifunction device such as a smartphone, or a computing device integrated within another device as a controller (for example, within a vehicle or on electrical equipment). The output of the user input device may be used for any appropriate purpose in software using any of these devices, from basic cursor movement to more complex functions such as handwriting input or drawing input in a graphics editing package.

The tremor detection module 32 is essentially a conventional user interaction layer—it receives input 41 from a physical input layer 31 such as a touchscreen (resistive, capacitive, optical etc.), a joystick, or a mouse—none of which requires any further discussion here as any appropriate conventional technology can be used, and the skilled person will be readily aware of how to construct an appropriate interface or repurpose an existing technology to provide one. The tremor detection module 32 extracts an output 42 from this physical input layer 31. Typically, a single output value from such a device is a position value—for a two-dimensional device, normally an (x,y) coordinate pair measured with respect to an origin, and the normal form of output is a time-ordered stream of values 43—typically, this will involve values measured at a predetermined sampling rate, but in principle explicit time values could be included, or measurements where there was no change in position could be ignored.

For the purpose of tremor correction according to an embodiment of the disclosure, adjacent values in the time-ordered set can be considered as connected by straight lines. This represents the entire user action as a series of small straight-line segments connecting adjacent points—this is a piece-wise linear model approximating the actual smooth movement of the user. Linear interpolation can be used to add additional point if needed for subsequent processes.

The tremor learning module 33 has two functions. One is to learn a specific user's tremor patterns to build a specific tremor model for the user—this is the training phase. The other is to provide a learned specific tremor model for the tremor cancellation module 34 to use in cancelling the associated user's tremor.

To allow the user input device to act to external systems exactly as a conventional user input device, it may be desirable to provide a physical mechanism—such as a button or catch—on the device to establish that it is in the "use" state or the "training" state. Otherwise, it may be necessary for there to be some software interaction at least with the computing device that will indicate that the user input device has a training state and a use state, complicating use and compromising user privacy. In the training phase, there will typically need to be interaction with an external computing device, as discussed below.

The training state will now be described in more detail with reference to FIGS. 5 to 8. The training state will typically be carried out as a one-time offline (in the sense that the user input device is not being used for other user input tasks for a computer system) phase—the intention is to personalise the user input device for a user so that tremor patterns for that user are cancelled. This phase may be repeated or extended to provide better results, or it may be carried out afresh for a different user to re-personalise the user input device for that new user. In theory, it would be possible for more than one user input profile to be stored so that the user input device could be easily used by any one of a plurality of users for which it had been trained.

In a first step, a training phase needs to be established 51 (with reference to FIG. 5)—this is distinguished from the "running phase" when the trained user input device is in use to provide tremor-cancelled input to a computer system using a model of the tremor patterns of the relevant user. As will be discussed below, it may be possible for such a model to be further refined during a running phase, but the present disclosure teaches at least an initial training phase to allow an effective model to be constructed.

In the training phase, it is necessary to obtain user input corresponding to a known output. To achieve this, it may be practical to run a user input device training programme on a computing device in connection with the user input device. This will be designed to provide the functionality indicated below, and to so to provide a process for establishing a user tremor model and installing it within the tremor learning module 33.

The programmed computing device and the user input device together form the training system.

Once the training phase has been established, the training system provides 52 the user with a number of predefined tasks—these may be a fixed set, or a subset of a larger set. Individual tasks may involve, for example, writing letters or figures from an alphabet, or drawing a simple polygon. The user input for each such task is captured 521 by the tremor detection module 32 as a time-ordered stream of position values which are then represented in the piece-wise linear form as described previously. A curve fitting approach (such as polynomial regression, or segmented regression) is carried out 522 on this input (either on the time-ordered set of user movement points ($x_i$, $y_i$) or on the piece-wise linear representation, depending on the technique). A high degree polynomial is constructed to provide the best fit to the user's actual input—typically such fitting approaches start with a first-degree polynomial and gradually increase higher order terms, increasing the degree of the polynomial to order m (where m is the order of the highest order term). This process may continue until the deviation error e (calculated by least squares or another appropriate means) falls below a suitably low value (say 0.001), at which point that task is sufficiently trained 523. A number of tasks will be trained using a similar approach—these may be all new tasks, or a user may in some embodiments be required to perform the same task more than once—and this process continues 53 until an appropriate number of tasks has been completed 54.

Figure 6:
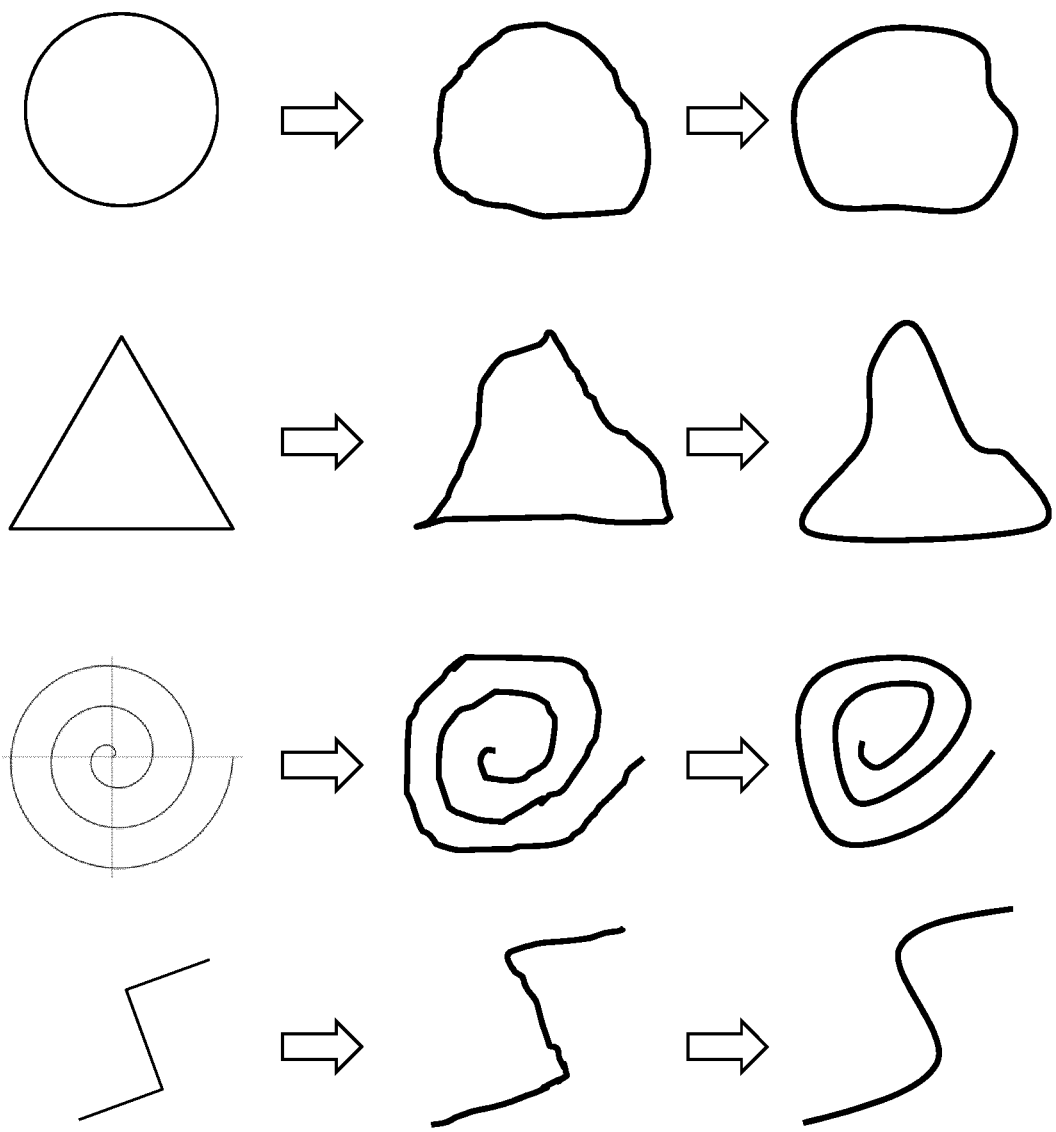
FIG. 6 illustrates representative outputs for the training module of FIG. 5.

FIG. 6 illustrates this approach. A number of task objects 61 are shown, with the user input 62 for each task object shown after this. The user input is then described as a high order polynomial 63 after a polynomial fitting process.

Figure 7:
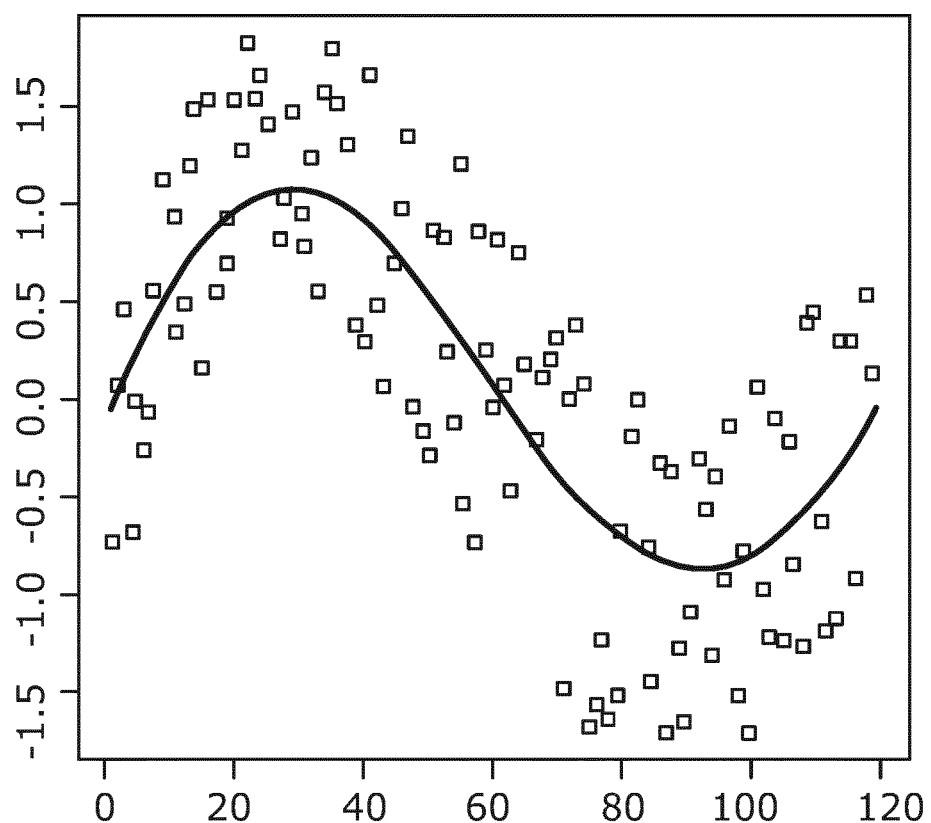
FIG. 7 illustrates an exemplary fitting process usable in connection with the approach of FIG. 5 using polynomial regression.

Polynomial regression (as illustrated in FIG. 7) has the form $$\hat{y}_i = \beta_0 + \beta_1 x_i + \beta_2 x_i^2 + \ldots + \beta_m x_i^m + \varepsilon_i \quad (i=1, 2, \ldots n)$$

expressed in matrix notation as $$\begin{bmatrix} \hat{y}_1 \\ \hat{y}_2 \\ \vdots \\ \hat{y}_n \end{bmatrix} = \begin{bmatrix} 1 & x_1 & x_1^2 & \cdots & x_1^m \\ 1 & x_2 & x_2^2 & \cdots & x_2^m \\ \vdots & \vdots & \vdots & & \vdots \\ 1 & x_n & x_n^2 & \cdots & x_n^m \end{bmatrix} \begin{bmatrix} \beta_0 \\ \beta_1 \\ \vdots \\ \beta_m \end{bmatrix} + \begin{bmatrix} \varepsilon_1 \\ \varepsilon_2 \\ \vdots \\ \varepsilon_n \end{bmatrix}$$

or $\hat{\vec{y}} = X\vec{\beta} + \vec{\varepsilon}$, where $e = \Sigma |\hat{y}_i - y_i|^2$ At this point, there exist a number of task objects and associated high level polynomial representations which correspond to the user's inputs in representing these task objects. The user's tremor pattern can be derived from these by machine learning. First of all, the tremor learning module 33 learns 54 for each task a mapping between the user input movements and the original object of the task. The characteristics of the obtained fitting curves—the degree and the coefficients—can then be used by a machine learning classification model to categorise the polynomial representation in association with the predefined object or shape associated with the relevant task. Multi-class perceptron (described generally at https://en.wikipedia.org/wiki/Perceptron) is one appropriate machine learning technique for learning mappings from fitted polynomials to training objects—support-vector machines (https://en.wikipedia.org/wiki/Support-vector machine) are another.

Considering the perceptron approach, learning can take place according to the following process. If a represents the set of input parameters (coefficients and degree of the polynomial) and b represents the output of the system (the target object), then a feature representation function $f(a,b)$ maps each possible input-output pair to a real-valued vector (the feature vector). A multiplicative weight factor w is applied with a score used to choose among the possible inputs, with $$\hat{b} = \mathrm{argmax}_b\, f(a,b) \cdot w$$

Iterating over the training examples, the weights are modified depending on the computed error as:

$$w_{t+1} = w_t + f(a,b) - f(a,\hat{b})$$

The final weights learned by the model are later used to combine the feature vectors for new inputs. For symbols that were part of the training set, weights are already established, but additional further symbols may also be interpreted based on their relationship to trained symbols—for example, as a combination of two already trained symbols. In cases where there is no clear identification, the user may be offered a choice from candidate symbols, so the user can choose the prediction that matches the user intent (this may in embodiments be used as a further training step). Where the input is not in the form of symbols to be recognised, but instead in the form of arbitrary shapes, the same combination of input from trained symbols (which may define for example how the user represents a straight line, or a curve of a particular type) can be used to provide a best prediction of arbitrary input. In general, however, the more training data obtained, and the more complex the shapes provided in the training data, the better the prediction will be for previously unseen symbols or arbitrary inputs.

Figure 8:
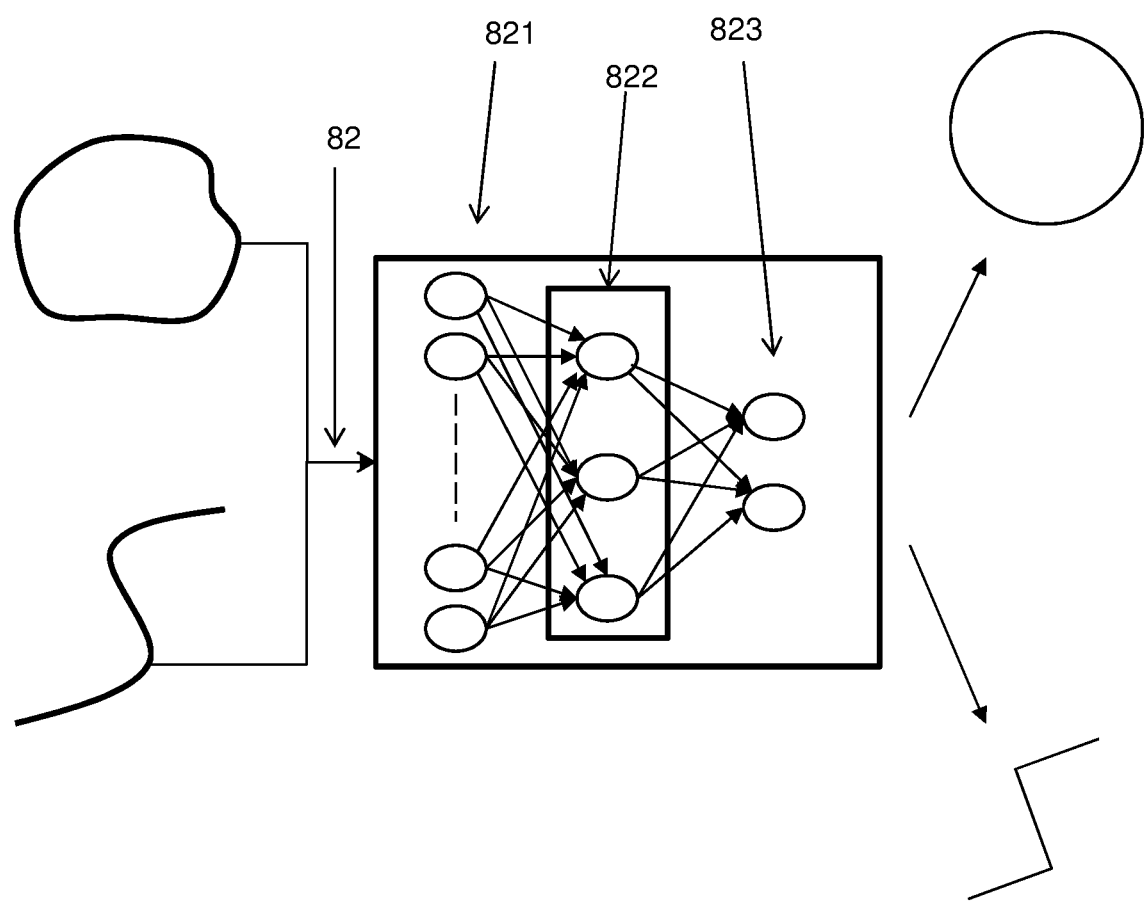
FIG. 8 illustrates a learning process used in a training phase in an embodiment of the disclosure.

Using this approach, a personalised model of tremor patterns is developed for the user—a personalization layer for the user. This is the output of the training phase. Typically, the set of tasks used in establishing the personalization layer will be pre-defined, in accordance with the complexity of shapes and objects that the system wishes to capture (this may, for example, be much more detailed and complex if the system needs to be trained for free drawing, and less complex if the system only needs to be trained to identify which of a number of discrete inputs the user is seeking to represent). FIG. 8 represents the model learning process—working from fitted polynomials 81, which are reduced to characterising inputs 82 (here, degree of the polynomial and the coefficients), to the machine learning process 83 (in this case, multi-class perceptron), which establishes correspondence with the test object 84.

The tremor pattern model for the user is used in the running phase by the tremor cancellation module to eliminate tremor from the user's input. As in the training phase, the user provides an arbitrary input to the system. These user movements are captured as (x,y) coordinates and transformed into a piece-wise linear representation. The module then computes (on the fly) a high-degree polynomial representation to approximate the user input, as previously described for the tremor detection module and tremor learning module respectively.

The characteristics of the fitted polynomial—the degree and the coefficients—are then passed through the personalization model for the user (the pre-trained classification model within the tremor learning module). This classification output is considered to be the actual action, object or shape that the user (with tremor condition) had intended to perform.

This output obtained from the classification framework (using machine learning to recognise the user's intended output) is then converted back into a normal digital representation of user movements—a series of screen coordinates to represent the intended user action. This is information of the same form as the output of the tremor detection module, but with tremor corrected for.

Figure 9:
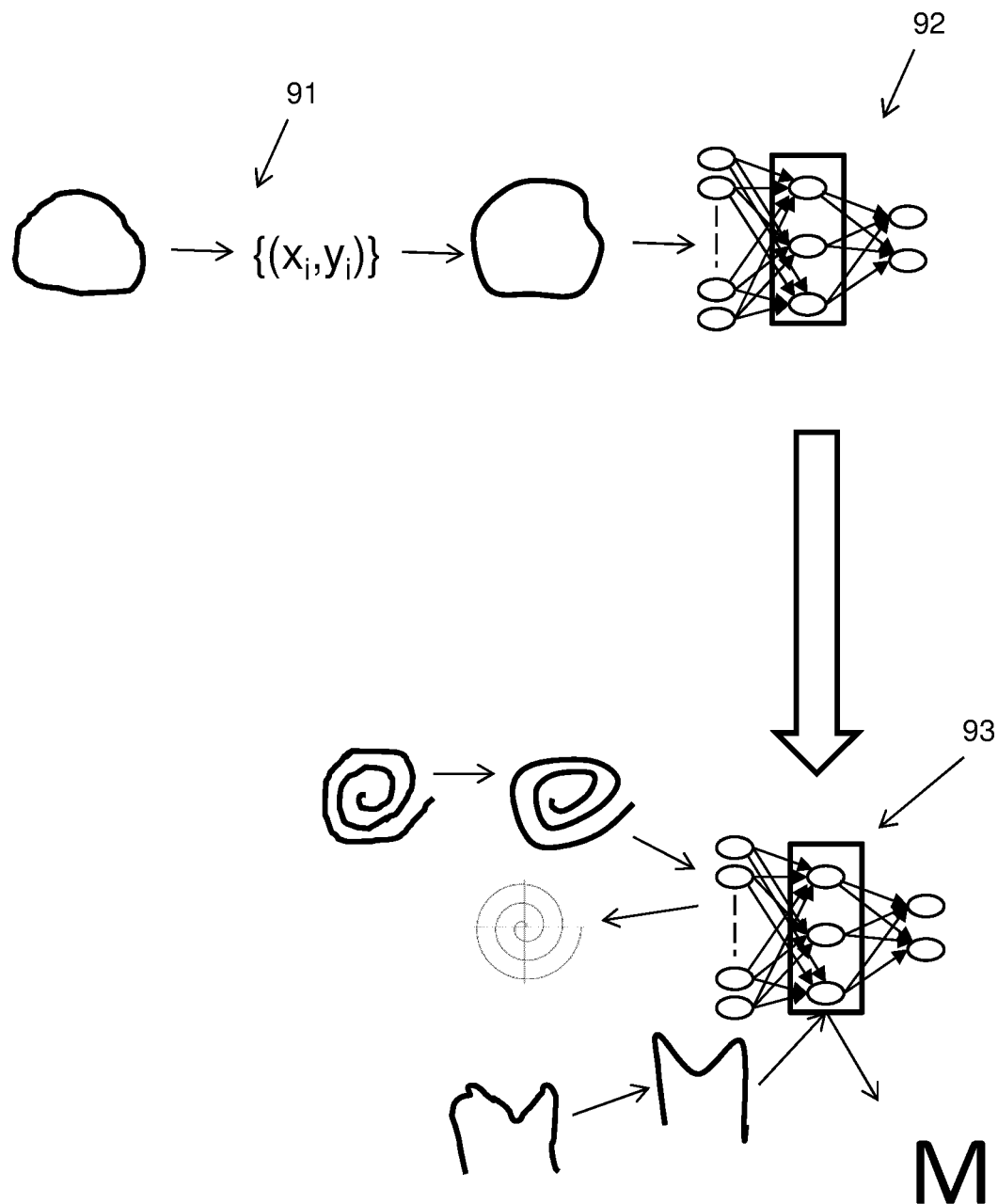
FIG. 9 illustrates stages of a full process from tremor learning and training to tremor cancellation according to embodiments of the disclosure.

FIG. 9 illustrates this full process. The tremor detection module provides user input representation 91—as bare user input converted into an (x,y) representation. In the training phase 92, the tremor learning module takes user input of this type for representations of various task objects, then it performs a polynomial fit and uses the polynomial parameters in a machine learning process to establish a personalisation layer. In the running phase 93, user input is fitted to a polynomial as before then provided to the trained model to determine the user's intended input—this is then rendered as (x,y) coordinates and provided as the output to the model.

In this way, the trained user input device provides output that corresponds to the output that would be produced by a conventional user input device used by that user if that user did not experience tremor. This allows the user to provide input to particular software—such as drawing and CAD software, for example—that does not reveal the user's tremor and reflects the user's intentions (it is both privacy-preserving and effective input).

The user input device itself can have a conventional appearance—it may comprise a small additional hardware component, such as a small additional circuit board, that may be hidden within an existing shell for a joystick or a mouse (or other input device), and may communicate with computing apparatus over Bluetooth or by wire in a conventional way. As tremor cancellation is provided entirely internally to the user input device after training, no additional connections to the computing device are needed, and the device driver can be the same as for a conventional user input device of the same type.

There are some external device types—such as a table top interactive display—where it will not be possible to provide user input by a mouse or joystick directly. However, a solution can be provided by projecting or sharing—via Bluetooth or another local networking technology—the surface of the screen and its contents on to a display associated with the user input device. User input may be provided in the way indicated above, and the user input provided in this way shared from the display associated with the user input device to the external device display. This allows a user with tremor to interact effectively with these devices. This approach can be used for providing drawing-type interactions but also keyboard inputs.

Other uses of embodiments of the disclosure are possible. One approach is simply the measurement of tremor and its development over time—a user may simply complete the training phase from an untrained state, and the resultant user tremor model compared to a user tremor model determined at an earlier time. This may be used to identify and understand progressive changes in a tremor condition.

As the skilled person will appreciate, the embodiments described above are exemplary, and further embodiments falling within the spirit and scope of the disclosure may be developed by the skilled person working from the principles and examples set out above.

The invention claimed is:

1. A user interface device for tremor cancellation, the user interface device comprising:
    a user interface for determining position data from physical user inputs produced by a user in order to move a cursor across a display;
    a tremor learning module comprising a machine learning model;
    a tremor cancellation module; and
    a position output,
    wherein the tremor learning module is adapted to be trained to identify tremor patterns for a user by comparing time-ordered streams of position data determined from physical user inputs produced by the user with predetermined representations of task objects,
    wherein the time-ordered streams are each fitted as a curve by a high-order polynomial and mapped to associated predetermined representations of task objects using the machine learning model,
    wherein the tremor cancellation module is adapted to apply the tremor patterns learned for the user to cancel tremors in a new time-ordered stream of position data determined from physical user inputs produced by the user to create a time-ordered corrected stream of position data which is corrected for user tremor, and
    wherein the position output is adapted for providing the time-ordered corrected stream of position data to move the cursor across the display.

2. The user interface device of claim 1, wherein the machine learning model is a classifier.

3. The user interface device of claim 2, wherein the machine learning model is a perceptron.

4. The user interface device of claim 1, wherein fitting the time-ordered streams to predetermined representations is provided by polynomial regression.

5. The user interface device of claim 4, wherein the input to the machine learning model comprises the order and the coefficients of the polynomial.

6. The user interface device of claim 1 comprising a single physical device.

7. The user interface device of claim 6, wherein the user interface device is a mouse.

8. The user interface device of claim 6, wherein the user interface device is a trackpad.

9. The user interface device of claim 6, wherein the user interface device is a joystick.

10. A method of cancelling user tremor with a user interface device, the user interface device comprising a user interface for determining position data from physical user inputs produced by a user in order to move a cursor across a display, the method comprising:
    training a tremor learning module comprising a machine learning model to obtain tremor patterns for the user by comparing time-ordered streams of position data determined from physical user inputs produced by the user with predetermined representations of task objects, wherein the time-ordered streams are each fitted as a curve by a high-order polynomial and mapped to associated predetermined representations of task objects using the machine learning model;
    applying the tremor patterns learned for the user to cancel tremors in a new time-ordered stream of position data determined from physical user inputs produced by the user to create a time-ordered corrected stream of position data which is corrected for user tremor; and
    providing the time-ordered corrected stream of position data to move the cursor across the display.

11. The method of claim 10, wherein the machine learning model is a classifier.

12. The method of claim 11, wherein the machine learning model is a perceptron.

13. The method of claim 10, wherein fitting the time-ordered output streams to the predetermined representations is provided by polynomial regression.

14. The method of claim 13, wherein an input to the machine learning model comprises an order and coefficients of the polynomial.

* * * * *